US006973338B2

(12) United States Patent
Isenberg et al.

(10) Patent No.: US 6,973,338 B2
(45) Date of Patent: Dec. 6, 2005

(54) CONJUNCTIVAL MONITOR

(75) Inventors: Sherwin J. Isenberg, Los Angeles, CA (US); Irwin Weiss, Los Angeles, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 278 days.

(21) Appl. No.: 10/316,168

(22) Filed: Dec. 9, 2002

(65) Prior Publication Data
US 2004/0111018 A1 Jun. 10, 2004

(51) Int. Cl.⁷ .............................................. A61B 5/00
(52) U.S. Cl. ...................................... 600/318; 600/356
(58) Field of Search ................................ 600/318–321, 600/356, 345, 348, 355, 361, 353

(56) References Cited

U.S. PATENT DOCUMENTS

| 4,524,776 | A | * | 6/1985 | Withers et al. ............. 600/383 |
| 5,127,077 | A | * | 6/1992 | Iyer et al. .................... 600/342 |
| 5,408,999 | A | * | 4/1995 | Singh et al. ................. 600/342 |
| 5,670,097 | A | | 9/1997 | Duan et al. |
| 6,031,603 | A | | 2/2000 | Fine et al. |
| 6,312,393 | B1 | | 11/2001 | Abreu |

OTHER PUBLICATIONS

Biography of LeLand Clark, "Clark Type Oxygen Electrode," www.chem.ch.huji.ac.il/ ~ eugeniik/history/clarkleland.htm (Oct. 4, 2002).
Caprette, David A., "Polarographic System For Measurement Of Dissolved Oxygen," www.ruf.rice.edu/ ~ bioslabs/studies/mitochondria/oxygraph.htm (Oct. 4, 2002).
Heyworth, J., "Conjunctival Oxygen Monitoring In The Initial Assessment Of Trauma," *Arch. Emerg. Med.*, 9(3): 274-9 (1992).
Isenberg and Shoemaker, "The Transconjuctival Oxygen Monitor," *Am. J. Ophthalmol.*, 95(6):803-6 (1983).
Isenberg, J., et al., "Continuous Oxygen Monitoring Of The Conjunctiva In Neonates," *Journal of Perinatology*, 22:46-9 (2002).
Nisam, M., et al., "Effects Of Hyperventilation On Conjunctival Oxygen Tension In Humans," *Crit. Care Med.*, 14(1):12-5 (1986).
Philips Medical Systems, "Trendcare Continuous Blood Gas Monitoring System Technical Overview With Paratrend And Neotrend," (2001).
Rank Brothers Ltd., "Dissolved Oxygen Electrodes," www.rankbrothers.co.uk/prod1.htm (Oct. 4, 2002).
Serdahl, C.L., et al., "The Effects Of Apraclonidine On Conjunctival Oxygen Tension," *Arch. Ophthalmol.*, 107 (12):1777-9 (1989).
Thermo Russell, "Measurement of Oxygen: Dissolved Oxygen Measurement Theory and Practice," www.thermorussell.com/techox.htm (Oct. 4, 2002).
Waxman, K., "Noninvasive Monitoring In Emcergency Resuscitation," *Am. Emerg. Med.*, 15(12):1434-6 (1986).

* cited by examiner

*Primary Examiner*—Eric F. Winakur
(74) *Attorney, Agent, or Firm*—Foley & Lardner LLP; Richard J. Warburg

(57) ABSTRACT

A method for monitoring blood/tissue gases, blood pH, and other elements of blood and tissue chemistry is described that uses a sensor tip that is placed adjacent to the conjunctiva of a patient to be monitored. Monitors and sensor using optical fiber sensors for performing the monitoring are also described.

58 Claims, 2 Drawing Sheets

CONJUNCTIVAL MONITOR

CROSS-REFERENCE TO RELATED PATENT APPLICATIONS

Not applicable.

BACKGROUND OF THE INVENTION

The present invention relates to the field of monitoring of blood gases and other blood parameters. The information provided and references cited herein are intended solely to assist the understanding of the reader and does not constitute an admission that any of the information provided or references cited constitute prior art to the present invention.

An important feature of current medical practice is the ability to monitor patients while they are in the hospital or otherwise undergoing intensive treatment. While a variety of different parameters can be monitored, important indicators of patient condition and response are provided by monitoring blood and tissue chemicals. As blood is responsible for the transport of oxygen and numerous other important molecules, blood and tissue analysis provides important information regarding the health status of an individual.

Thus, measurement of pH, which reflects the acid base status of tissue, carbon dioxide tension ($PCO_2$), and oxygen tension ($PO_2$) are some of the important markers used by clinicians to determine the well being of patients. Currently a typical blood gas analysis consists of these three measurements. These values reflect oxygenation and ventilation of the patient as noted in arterial blood. The arterial blood gas, however, does not indicate tissue perfusion.

Tissue perfusion is important because in certain vital organs, especially the brain, poor tissue perfusion can lead to permanent damage. There has been much work done over the years to measure brain perfusion. These techniques unfortunately utilize large bulky equipment that is extremely expensive, such as with Positron Emission Tomography, or are invasive and require placement of a catheter within the brain or other vital organs.

Most blood analyses have utilized invasive methods such as those utilizing needles to draw blood for further laboratory analysis. Other invasive methods utilize sensors that are inserted into a blood vessel, e.g., into an artery to measure arterial blood parameters. An example of such a sensor system is provided by Philips Medical Systems as the Trendcare Continuous Blood Gas Monitoring System, utilizing in vivo intra-arterial sensors. The in vivo sensor is inserted through an arterial catheter and allows monitoring of pH, oxygen, carbon dioxide and temperature. The sensors utilized for the pH, oxygen and carbon dioxide determinations are optical fibers that include perforations containing indicator solutions at the tips. The sensor also includes a thermocouple for temperature determinations. In use, the sensor tip is extended approximately 2.5 centimeters into the artery in which the catheter is placed.

Non-invasive methods for determination of oxygen and glucose have also been described. One method, the pulse oximeter method, utilizes near-infrared absorption spectroscopy and indirectly measures arterial blood oxygen through the skin. Sensors are placed over the skin with LEDs emitting light at two wavelengths, with peaks of approximately 940 and 660 nanometers respectively. As the blood oxygenation changes, the ratio of the light transmitted by the two frequencies changes, indicating the amount of oxygenated hemoglobin in the arterial blood, e.g., at a fingertip.

A device for detecting glucose at the conjunctiva of the eye has been described in Abreu, U.S. Pat. No. 6,312,393, issued Nov. 6, 2001, entitled Contact Device for Placement in Direct Apposition to the Conjunctive of the Eye. The Abreu glucose sensor described is an electrochemical sensor, and has an enzyme electrode mounted inside a contact device in contact with the tear fluid or surface of the eye. The sensor measures the "oxidation current of hydrogen peroxide created by the stoichiometric conversion of glucose and oxygen in a layer of glucose oxidase mounted inside the contact device." (Abreu, col. 29, lines 49–51.) Thus the "glucose enzyme electrode responds to changes to the concentration of both glucose and oxygen, both of which are substrates of the immobilized enzyme glucose oxidase. It is also understood that the sensor in the contact device can be made responsive to glucose only by operating in a differential mode." (Abreu, col. 29, lines 57–62.) Abreu also indicates that "optical sensors mounted in the contact device can evaluate oxygen and other gases in tissues and can be used to detect the concentration of compounds in the surface of the eye." (Abreu, col. 17, lines 27–30.) It further indicates that "optical, acoustic, electromagnetic, micro-electromechanical systems and the like can be mounted in the contact device and allow the measurement of blood components in the tear film, surface of the eye, conjunctival vessels, aqueous humor, vitreous, and other intraocular and extraocular structures." (Abreu, col. 17, lines 33–38.) A described sensor utilized a needle type glucose sensor. Another described sensor used a rod-shaped device in which a sensor surface is held directly against the surface of the eye. Other described devices were similar to contact lenses or a portion of such a lens, e.g., an annular ring. Preferred embodiments for such glucose sensors utilized transmitters to avoid wire connections outside the eye.

A transconjunctival oxygen monitor was described in Isenberg and Shoemaker (1983) *Am. J. Ophthalmol.* 95:803–806. This oxygen monitor was based on a Clark electrode mounted on a polymethacrylate conformer and was intended to continuously measure the tissue oxygen tension of the palpebral conjunctiva. A Clark electrode is an electrochemical electrode that utilizes two half cells separated by a salt bridge. Oxygen diffuses through a membrane (e.g., polypropylene or Teflon) into a chamber containing potassium chloride solution. Also in the chamber are two electrodes, one a reference silver/silver chloride electrode and the other is a platinum electrode. The electric current between the two electrodes when polarized with a negative potential (e.g., −600 mV vs. Ag/AgCl) indicates the oxygen concentration in a solution. (The electrode can be used to measure the hydrogen concentration instead of the oxygen concentration by using a positive voltage.) Such Clark electrodes are thus polarographic electrodes.

Likewise, Waxman (1986) *Ann. Emerg. Med.* 15:1434–1436, described a non-invasive monitoring in emergency resuscitation where the "transcutaneous oxygen (TtcO2) monitoring technique uses a Clark electrode applied noninvasively to the skin surface." Similarly, Nissan et al. (1986) *Crit. Care Med.* 14:12–15, indicated that a "polarographic conjunctival oxygen sensor was used to measure oxygen tension in a tissue bed supplied by the internal carotid artery", and further indicated that "[t]he shared vascular source of the conjunctiva and brain suggests that conjunctival PO2 monitoring may provide an index of cerebral perfusion.

SUMMARY OF THE INVENTION

The present invention concerns the detection of blood and tissue gases and other parameters, preferably multiple gases, using a monitor that includes a sensor placed adjacent to the conjunctiva in a patient's eye. It was found that a sensor in that location can continuously monitor gases such as oxygen and carbon dioxide, as well as pH and temperature. The conjunctival monitor detects the particular gases and pH that result from diffusion from the conjunctiva, e.g., from the blood in blood vessels in the conjunctiva. Those gas and/or pH values thus provide indicators of those parameters in local tissues, especially in the brain. This allows such important indicators of patient condition and treatment response to be tracked without the need for an invasive procedure to place an internal monitor, such as is required for an arterial blood gas monitor.

Thus, in a first aspect the present invention provides a method for monitoring blood and tissue parameters, e.g., blood gases, by placing a sensor of a conjunctival monitor adjacent to the conjunctiva in the eye of a patient, and determining values for the measured blood parameters. In many cases, blood gas values will be determined, which in preferred embodiments are for a plurality of gases. Typically the monitoring will be carried out over a period of time, usually with continuous monitoring, though periodic or intermittent monitoring can also be performed. The blood gas and/or other blood parameter values will be displayed in some form and/or recorded. While such monitoring can be performed on any patient, it is particularly advantageous for patients who are undergoing treatment, such as surgical procedures, that can compromise brain and/or cardiac and/or lung function, and for patients who have compromised cardiac and/or lung function and are treated to improve or stabilize those functions. Additional patient parameters that can be measured include blood pH and temperature, among others.

Advantageously, the method can utilize a conjunctival monitor sensor that uses an optical fiber sensor or sensors, and can include other types of sensors such as electrode sensors and thermocouples (for temperature determination). In particular embodiments, the sensor has a sensor tip with a detection length of 2 cm or less adapted to fit adjacent the conjunctiva of a patient's eye; the sensor tip includes an exterior, biocompatible, microporous membrane containing at least two of a pH optical sensor fiber, a $PCO_2$ optical sensor fiber, and a $PO_2$ optical sensor fiber, where fluid flow through the microporous membrane is inhibited; the sensor tip also includes a distal terminal mirror that returns light through one or more of said optical sensor fibers; the detection length is 1.9, 1.8, 1.7, 1.6, 1.5, 1.4, 1.3, 1.2, 1.1, or 1.0 cm or less; the sensor includes a pH optical sensor fiber, a $PCO_2$ optical sensor fiber, and a $PO_2$ optical sensor fiber; the sensor also includes a temperature sensor, that can include a thermocouple; fluid flow inside the sensor is inhibited, such as with a gel, e.g., polyacrylamide gel; fluid flow in contact with sensor fibers or electrodes is restricted; a plurality of sensor fibers are bundled together within an outer covering, such as an outer membrane; the sensor tip is coated with heparin; optical sensor fibers include one or more acrylic optical fibers; a pH optical sensor fiber includes phenol red in polyacrylamide gel, such as in perforations in the fiber; a $PCO_2$ optical sensor fiber includes phenol red in bicarbonate solution, such as in perforations in the fiber; a $PO_2$ optical sensor fiber includes ruthenium dye in a silicone matrix, such as in perforations in the fiber; perforations in a sensor optical fiber are square or rectangular; perforations are laser drilled; perforations are arranged in a helical pattern; a sensor includes pH optical sensor fiber that includes phenol red in polyacrylamide gel, a $PCO_2$ optical sensor fiber that includes phenol red in bicarbonate solution, and a $PO_2$ optical sensor fiber that includes ruthenium dye in a silicone matrix, and the fibers are perforated with the respective indicator solutions in the perforations; the oxygen sensor is not a polarographic electrode such as a Clark electrode; the sensor individually detects a plurality of different gases, for example, 2, 3, or 4 different gases; the sensor tip is adapted to fit in the formix.

In general, the monitoring method is carried out using a monitor system. The monitor includes a sensor as described herein. In particular embodiments of monitors, the monitor includes a light source and photodetectors; green light pulses are used for detection and red light pulses are used for reference in pH and $PCO_2$ optical sensor fibers, and blue light is used for detection and green light is used for reference in a $PO_2$ optical sensor fiber; temperature readings from a temperature sensor are used to normalize readings for one or more of pH, $CO_2$, and $O_2$ to a standard temperature, such as 37° C.; the monitor includes an analysis unit that processes signals from said sensor tip and converts those signals into output representative of blood/tissue gas or blood/tissue pH values or both; the monitor includes a display unit for displaying output for blood/tissue gas and/or pH values; sensors are calibrated, such as using one or more defined gas mixtures to equilibrate a liquid.

In certain embodiments, the monitoring is conducted during treatment of a patient; in monitoring during treatment, patient treatment includes a surgery such as heart surgery, lung surgery, brain surgery; in monitoring during treatment, the patient treatment involves injection or infusion of a drug; monitoring is performed for a period of at least ½, 1, 2, 4, 6, 8, 12, 18, or 24 hours, or even longer; monitoring is carried out in an intensive care unit; monitoring is carried out in an emergency room; monitoring is carried out in an emergency vehicle; monitoring is carried out on a patient who has had accidental blood loss such that the patient is at risk of insufficient tissue perfusion, such as a victim in a vehicle accident (e.g., car, truck, boat, train, airplane); monitoring is carried out on a neonate, who can be premature; monitoring is carried out on a child undergoing surgery; the sensor tip is place in the fornix for monitoring.

In particular embodiments, the method involves placing an optical blood/tissue gas monitor sensor tip adjacent the conjunctiva of a patient (preferably in the fornix), where the sensor tip includes at least one optical sensor fiber for detecting at least one blood/tissue gas (e.g., oxygen, carbon dioxide, and/or other gases for which microsensors are available) or blood/tissue pH and the sensor tip is connected with analysis and display components of a blood/tissue gas monitor system; monitoring patient blood/tissue gas or pH values from the sensor tip; and recording or displaying (or both) the patient blood/tissue gas and/or pH values; the sensor includes a sensor fiber or electrode for any one of sodium, potassium, lactate, nitrogen, or any combination, such sensor or sensors can also include one or more of an oxygen sensor, a carbon dioxide sensor, a pH sensor.

As the conjunctival monitoring is reflective of cerebral perfusion, the invention also provides a method for monitoring brain perfusion by performing conjunctival monitoring as described herein, where the sensor contains at least an oxygen monitor and oxygen levels are monitored.

In a related aspect, the invention thus provides a conjunctival blood/tissue gas monitor that provides simultaneous monitoring of multiple blood gases. The monitor can be configured to also monitor additional parameters, for example, pH, temperature, sodium, potassium, and/or lactate. In particular embodiments, the monitor includes a sensor as described herein, that includes one or more optical sensors, e.g., as described herein.

Likewise, the invention provides a sterile, packaged conjunctival sensor that includes a written indication that the sensor can be used as a conjunctival sensor. The sensor is as described herein, and is packaged such that at least the portion of the sensor that will be placed in a patient's eye, and preferably all of the sensor, is enclosed in sterile packaging. In certain embodiments, the sensor is a disposable (single use) conjunctival blood/tissue gas sensor. Preferably the sterile sensor includes optical sensor fibers; optical sensor fibers are adapted for monitoring of oxygen, carbon dioxide, and/or pH, and preferably also includes a thermocouple for temperature determination. The sterile packaging can be of a type recognized by those skilled in the art as suitable for sterile packaging of medical devices, such paper and/or plastic packaging. The written indication that the sensor can be used at the conjunctiva can be placed on a portion of the sensor, on an attachment to the sensor, on the packaging and/or on a separate item, e.g., a separate sheet of paper packaged with the sensor; the written indication can indicate that the sensor tip is placed in the fornix. The packaging is preferably of a type approved for packaging of small medical devices.

In the context of this invention, the term "sensor" refers to a component of a monitor or analyte detection system that is placed at the detection site and produces a signal indicative of the parameter(s) being detected (e.g., the level of analyte or the temperature). This does not mean that no other components are involved in generating the signal. For example, it may be necessary to provide light or electrical current to the sensor, but the sensor produces an alteration in response to environmental condition, thereby producing the signal. A sensor will contain one or more specific parameter sensors (such as optical sensor fibers), such as an oxygen sensor or a carbon dioxide sensor. When the individual parameter sensors are intended, reference is made to the specific parameter that individual sensor is adapted to detect, e.g., oxygen sensor. Reference to "sensor" generally without such term modification means the entire component that is placed at the detection site.

As used herein, the term "monitor" or "monitor system" refers to a system for generating a signal or signals corresponding to one or more physiological parameters and using those signals to provide indications of those parameters, e.g., by displaying or printing values for the physiological parameter. The monitor is adapted to generate and detect such signals over a period of time, either continuously or a various times during the period without replacement of any components.

The term "conjunctiva" has its usual physiological meaning, referring to a mucous membrane that lines the inner surfaces of the eyelids and folds back to cover the front surface of the eyeball, except for the central clear portion of the outer eye. The conjunctiva is composed of 3 sections, the palpebral conjunctiva covering the posterior surface of the eyelids, the bulbar conjunctiva that coats the anterior portion of the eyeball, and the fornix, which is the transition between the posterior eyelid and the eyeball.

As used herein in connection with patient monitors, the term "conjunctival" indicates that the sensor or other specified component is adapted for placement adjacent to the conjunctiva of a patient's eye. Thus, the component does not damage the conjunctiva, eyeball, or other tissue of a normal person to an extent that would be clinically unacceptable. The component can also be curved or otherwise shaped to fit adjacent to the conjunctiva, e.g., curved to follow the curvature of the eyeball or to fit in the fornix.

In connection with the present sensors and their use in monitoring values for various parameters, e.g., oxygen, carbon dioxide, and pH, the term "blood/tissue" and "blood and tissue" indicate that such chemical parameters measured at the conjunctiva reflect diffusion from the local tissue and blood vessels in that tissue. This is distinguished from direct blood monitoring, such as arterial blood monitoring, in which a sensor is placed directly in the blood within a blood vessel. Unless clearly indicated to the contrary, in the context of the present conjunctival sensors, monitors, and methods, reference to a "blood gas sensor" or "blood gas monitor" and like terms mean "blood/tissue sensor" or "blood/tissue monitor".

As used in reference to the movement of bulk fluid within a sensor, the term "inhibited" or "restricted" or terms of like import indicate that bulk flow is sufficiently limited that diffusion transport predominates over bulk fluid transport for movement of small molecules, ions, and atoms (less than 300 daltons) in the region or conditions specified as having inhibited or restricted fluid flow. Preferably, transport by bulk flow will be less than 20%, 10%, or 5% of the flux via diffusion for a relevant chemical species.

In the context of blood/tissue gas sensors, the term "optical sensor" refers to a sensor for determining the tension or concentration of a dissolved gas using a spectroscopic detection method, e.g., a change in absorption of light having a particular wavelength or range of wavelengths. The exemplary optical sensors described herein use optical fibers to direct the illuminating and return light. Such an optical sensor using one or more optical fibers for detection of a particular analyte is referred to herein as an "optical fiber sensor".

The term "sensor tip" is used to refer to the terminal portion of a conjunctival sensor that is placed in the eye. The external portion of a sensor tip may differ from the exterior portions of a sensor that connect the tip to other components of a monitor system. The sensor tip includes the detection region in which reactions providing indications of parameters being measured occur, e.g., regions in which indicator solutions are present.

As used in connection with a sensor tip, the term "detection length" or "detection region" refers to the length or region of a sensor that is placed in the detection location and that is active in performing the detection. This does not, for example, include the portions of a sensor that connect the sensor tip with the other components of a monitor.

The term "optical sensor fiber" refers to a single optical fiber in an optical sensor that includes the chemical components for performing a particular detection, e.g., an oxygen tension, carbon dioxide tension, or pH determination. Multiple optical sensor fibers can be included in a single sensor.

The term "microporous" as used in connection with a material such as a membrane or sheath indicates that the material is penetrated with small holes or passages. In most cases, such holes are large enough to permit passage of a species that is to be measured, e.g., protons and/or dissolved oxygen and carbon dioxide. In some cases, such holes in a microporous material can also be sufficiently large to allow passage of water unless the holes are blocked, e.g., with a gel that has pores sufficiently small to inhibit passage of water.

Usually, such holes will be 0.5 mm or less, preferably 0.3, 0.2, 0.1, 0.05 mm or less, or even smaller, e.g., 30, 20, 10, 5 microns or less.

Additional aspects and embodiments will be apparent from the following Detailed Description and from the claims.

DETAILED DESCRIPTION OF THE PREFERRED EMBODIMENTS

Figure 1:
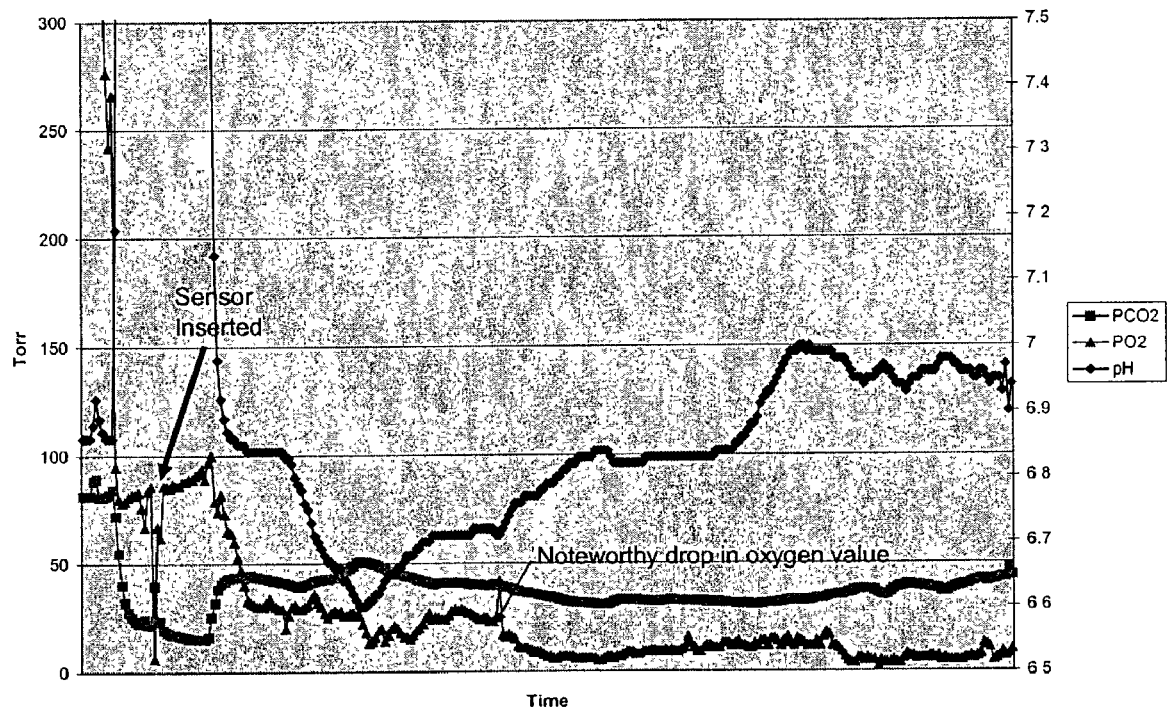
FIG. 1 is a graph showing the values for oxygen, carbon dioxide, and pH for exemplary patient 1, illustrating monitoring of low oxygen values.

As indicated in the Summary above, the present invention concerns the use of a conjunctival monitor for monitoring a patient's blood/tissue gases, and can also be configured to monitor other blood/tissue parameters such as pH, among others. Identification as a conjunctival monitor means that the system detects physiological parameters at the conjunctiva of the eye. The conjunctiva is a mucous membrane that lines the inner surface of the eyelids and folds back to cover the front surface of the eyeball, except for the central clear portion of the outer eye, the cornea. The conjunctiva is essentially transparent and is composed of three sections, the palpebral conjunctiva that covers the posterior surface of the eyelids, the bulbar conjunctiva that coats the anterior portion of the eyeball, and the fornix, which is the transition portion from the palpebral conjunctiva to the bulbar conjunctiva.

In the present system, a sensor is placed adjacent to the conjunctiva of the eye, e.g., at the fornix, and detects the relevant parameters. For example, such a monitor can measure oxygen tension, carbon dioxide tension, and pH, along with temperature. The sensor placed adjacent to the conjunctiva in a patient's eye can remain in place for extended periods of time, e.g., a period of hours or even longer. The sensor is used as part of a monitor system, that typically also includes a display, e.g., a screen and/or an output printer, and can also include electronic memory to store results, and/or a connection to a separate computer for storage and for processing of monitored parameters.

The present monitors can be used in many clinical cases, for example, in the emergency room to screen for perfusion of the brain in patients presenting in shock or having significant trauma. Likewise, patients with severe cerebral vascular accidents (strokes) can have their gas exchange monitored from their eye as a marker of severity and response to therapy directed against the clot in the brain. Also, for patients with severe respiratory failure in the intensive care unit, the gas exchange from the conjunctiva can be monitored as a marker for adequate oxygenation and perfusion of the brain. Likewise, the monitor can be used for patients that are or appear to be at risk for stroke, myocardial infarct, cardiac arrhythmia, cardiac afibrillation, and the like, as well as for patients in sickle cell crisis, and patients undergoing anaesthesia. Thus, the present conjunctival monitors provide a very beneficial method for assisting in caring for patients.

An example of an advantageous monitor system uses a thin, short sensor tip that includes optical fiber sensors, along with a light source for directing light into the optical fibers in the sensor, and photodetectors that detect light alterations in the returning light. Those differences between the incident and return light are analyzed to provide resulting values for the parameters that are being determined, e.g., oxygen, carbon dioxide, and pH. However, monitor systems can also be configured in other ways.

Conjunctival Sensor Design

A sensor for use in the present monitors should be configured to be suitable for placement adjacent to the conjunctiva of the eye of a patient without causing clinically unacceptable damage. Thus, the sensor tip should be short and thin (and highly preferably flexible), and constructed in a manner that will minimize damage to the conjunctiva or cornea. To accomplish this, the outer surface of the sensor tip should be a biocompatible material(s), with no hard or abrasive edges or protrusions. Preferably the outer surface of the sensor tip is not a hard material. The outer surface can further be coated with a material that renders or assists in making the sensor surface biocompatible, such as a heparin coating. Preferably the sensor will have a thickness of no more than 1 mm, more preferably no more than 0.7, 0.5, 0.4, or 0.3 mm.

Further, the sensor tip should be relatively short, preferably no more than 2 cm, more preferably no more than 1.7 cm, 1.5 cm, 1.3 cm, 1.0 cm, or even less. In this way, the sensor tip can fit adjacent to the conjunctiva in the eyes of most patients without extending so far that it pokes into the fornix or other locations around the eye. In addition, it is desirable that the sensor tip conforms to the curvature of the eye, e.g., to avoid damage to the conjunctiva and/or cornea. Thus, the sensor tip can advantageously be curved and/or the tip can be flexible.

The sensor tip can also be shaped in various ways. For example, the tip can be round, e.g., in the shape of a wire, or flattened, e.g., with a sensor width that is at least 2, 3, 4, 5, 10, or more times the thickness. Such flattened sensor tips can be formed using methods selected as suitable for the material used, e.g., cast or molded. Thus, for example, optical fiber or electrode sensors can be molded into the sensor tip outer coating in the desired shape. For sensors that include a plurality of sensor fibers, the fibers can be bundled so that individual fibers are in a common space in the sensor, or can be separated into two more separate bundles and/or separate fibers. Separation of fibers in this manner can, for example, allow utilization of sensor chemistries that are not compatible when used in a single space where signficant diffusion will occur from one to the other. Those skilled in the art are familiar with various fabrication methods, e.g., such as those used for fabricating contact lenses, both soft and rigid contact lenses, and can readily adapt such methods to the present sensor tips.

As indicated above, a preferred sensor tip will usually contain a plurality of different sensor fibers and/or electrodes, adapted to monitor a plurality of different blood gases, and can also monitor other analytes. Examples of blood gases of particular interest can include oxygen and carbon dioxide. Other analyses of interest include, for example, pH, temperature, sodium, potassium, nitrogen, and lactate. When a plurality of sensor fibers or electrodes are used, it can be advantageous to bundle or otherwise incorporate them in a single sensor. This is especially advantageous for the sensor tip, so that only a single sensor is placed in the eye. Such bundling can be accomplished with a variety of different structures, but should allow penetration of analytes that are to be detected when the sensor fibers, electrodes, or thermocouples are contained within a bundling structure. An exemplary sensor uses a microporous membrane surrounding the plurality of sensors. For example, such a sensor can include optical fiber sensors for monitoring oxygen, carbon dioxide, pH, and temperature, e.g., using exemplary sensor fibers and a temperature thermocouple as described below. The microporous membrane (e.g., polyethylene) allows diffusion of oxygen, carbon dioxide, and protons into the sensor such that those analytes can contact the sensor fibers. In certain embodiments, the membrane containing the sensor fibers and thermocouple is filled with a gel (e.g., polyacrylamide gel) that blocks the holes in the membrane so that diffusion instead of fluid transport predominates to carry the analytes to the sensor fibers. The pores in the gel are sufficiently small that bulk transport of water through the gel is minimal. The gel can also immobilize an indicator solution, such as an aqueous dye solution, for example, a phenol red solution used as the pH indicator in the exemplary pH sensor fiber described below. Such a sensor with an outer membrane can be produced using conventional methods.

Carbon Dioxide ($PCO_2$) Sensor

As discussed above, an example of a useful sensor is a carbon dioxide sensor. In general, such a sensor will detect the carbon dioxide ($CO_2$) tension at the conjunctiva. As the conjunctiva has only a very thin layer over the blood vessels, the $CO_2$ tension detected will effectively be that in the blood in the conjunctival blood vessels and tissue. A number of different sensor types can be used for monitoring $CO_2$, including, for example, an optical fiber using optical absorption that depends on the concentration of dissolved $CO_2$. An exemplary optical fiber for detecting $CO_2$ can be constructed as follows:

As indicated, an exemplary carbon dioxide sensor (i.e., a $PCO_2$ sensor) utilizes optical absorption. $CO_2$ sensitive changes in optical absorption are obtained by using a pH indicator dye in a fixed concentration sodium bicarbonate ($HCO_{3-}$) solution inside a gas permeable membrane. The gas permeable membrane, e.g., polyethylene, encloses an optical fiber and the indicator solution. The optical fiber has perforations, preferably through holes, that allow indicator solution to be in the light path in the optical fiber. For example, a fiber can have a plurality of through holes arranged in a helical fashion, so that essentially all (or at least most) of the light passing through the fiber will pass through at least one through hole containing indicator solution. Such holes can be made using a high intensity laser. Preferably the holes are square or rectangular with opposing flat surfaces perpendicular to the axis of the fiber.

In this system, $CO_2$ reacts with sodium bicarbonate, releasing protons, thereby making the solution more acidic. As a result, the greater the diffusion of $CO_2$ into the dye solution, the lower the pH. The fixed concentration of sodium bicarbonate in the solution can be pre-selected so that the system has sensitivity over the needed concentration range when used with the selected indicator dye. The intensity of light that is transmitted through the indicator is affected by the local pH.

While a number of different pH indicator dyes are known and can be used, an exemplary dye is phenol red indicator dye. The phenol red/sodium bicarbonate solution thus fills the holes of the optical fiber as described above. The gas permeable membrane providing gas selectivity can surround only the $CO_2$ sensor fiber, or can surround a sensor fiber bundle.

The sensor tip also includes a mirror to return light back through the optical fiber. Thus, to utilize the sensor tip and to carry out the monitoring, light is transmitted down the fiber, and return light (after passing though the indicator solution in the holes in the fiber) is analyzed to indicate the level of dissolved $CO_2$. While various light sources can be used, light emitting diodes (LEDs) provide a useful light source. The system also includes photodetectors (PDs) for detecting light returned through the fiber. In the exemplary system, pulses of green light, with a peak at 555 nm, are directed into an optical fiber (more than one fiber could be used). This fiber (carrying the incident light) is paired with another fiber(s) for carrying return light to a photodetector. The pair of fibers are matched with a single sensor fiber at an optical or electro-optical connector. Thus, the light is transmitted through the incident light fiber to the connector, and then down the single sensor optical fiber to the sensor tip where it passes through the holes containing the indicator solution.

In the exemplary system using phenol red as the indicator dye and green light pulses for detection, a portion of the incident green light is absorbed by the indicator solution in the light path of the optical fiber. The non-absorbed light is then reflected by a terminal mirror, back through the optical fiber and again through the detection zone containing the indicator solution such that additional absorption can take place. The non-absorbed green light returns through the optical fiber to the connector, where approximately ½ of the returned light is directed to the photodetector (the other ½ returns along the other optical fiber to the light source).

In using this sensor, $CO_2$ from the blood in the capillaries in the conjunctiva rapidly equilibrates with the indicator solution in the sensor fiber. Higher $PCO_2$ results in increased acidity of the indicator solution (lower pH). This causes a reduction in absorption of the green light. Light at a different wavelength (not significantly absorbed by the indicator dye) is also used for control purposes. In the exemplary system, red light pulses (preferably with a peak at 660 nm) are also directed down the optical fiber, e.g., between the green pulses. Because the red light is not significantly absorbed by the phenol red indicator dye, the returning red light can be used as a reference for the overall optical efficiency of the sensor fiber and associated components. Alterations in optical efficiency can be caused, for example, by variations in fiber quality, bending of the fiber, and by variations in dye concentration.

Oxygen ($PO_2$) Sensor

An exemplary oxygen sensor ($PO_2$), like the exemplary carbon dioxide sensor described above, is an optical sensor with indicator in through holes in an optical fiber. However, the exemplary $PO_2$ sensor utilizes fluorescence quenching rather than simple absorption. In fluorescence quenching, the intensity of a light emission from a fluorophore is reduced in the presence of oxygen. While a variety of fluorescent dyes are known, the exemplary system uses (tris (4,7 diphenyl-1, 10-phenanthroline) ruthenium III chloride). Similar to the $PCO_2$ sensor fiber described above, the $PO_2$ sensor fiber has through holes or perforations, preferably square or rectangular and preferably perpendicular to the fiber axis. The fluorescent dye is immobilized in a matrix, e.g., a silicone matrix that fills the holes in the optical fiber.

The $PO_2$ sensor fibers, light sources and photodetectors are configured in essentially the same manner as for the exemplary $PCO_2$ system described above, except that light of a different wavelength is used. Light pulses preferably with a peak at 465 nm, e.g., from a blue LED) are directed down an optical fiber, which is matched with another fiber for return light. In the sensor tip (or detection zone), the blue light enters the matrix containing the fluorescent dye. The blue light interacts with the fluorescent dye in the holes in the fiber, resulting in a fluorescent emission with a peak at 615 nm red fluorescence. The fluorescent light is emitted essentially isotropically, with the result that only a portion of the emitted light is directed within the optical fiber.

The blue light that does not interact with fluorescent molecules in the first pass through the detection zone is reflected through the detection zone again by a terminal mirror, resulting in increased fluorescent intensity, i.e., a stronger signal. The red fluorescent light that has been directed into the optical fiber (as well as the blue light that did not interact with a fluorescent molecule) returns in the optical fiber to the electro-optic connector, where approximately ½ of the light is directed through the fiber that goes to the photodetector and the other approximately ½ returns through the incident light fiber.

As noted above, in this system, the return light includes both the red fluorescent signal, and the residual blue light. In order to detect the fluorescent signal, the return light is passed through an optical filter (e.g., a band-pass filter) that is placed in the light path of leading to the photodetector, e.g., the filter is placed in front of the photodetector. The filter passes the red fluorescent signal, but blocks the blue light, so that the photodetector receives only the fluorescence signal.

Also similar to the exemplary $PCO_2$ system described above, oxygen from the blood in the conjunctival blood vessels equilibrates rapidly with the matrix containing the fluorescent dye, such that the higher the oxygen concentration, the greater the fluorescence quenching. Thus, the intensity of the fluorescent signal decreases with increasing oxygen concentration.

As in the $PCO_2$ system, it is also advantageous to use light of a frequency that does not significantly interact with the indicator solution in the matrix, and thus is transmitted essentially independently of the concentration of oxygen, as a standard controlling or allowing standardization for system efficiency. Thus, in an exemplary system, pulses of red light (preferably with a peak at 600 nm are also directed down the fiber, timed between the pulses of blue light. Such pulses can, for example, be from a red LED. In this system, the ratio of intensities of blue light to red light (from the fluorescent emissions) measures oxygen concentration because it measures the oxygen concentration-dependent fluorescent emission intensity.

pH Sensor

As with the exemplary oxygen and carbon dioxide sensors described above, an exemplary pH sensor uses an optical fiber. A helical set of rectangular holes perpendicular to the axis of the fiber perforates the fiber tip in the detection region.

The exemplary pH sensor is quite similar to the $CO_2$ sensor described above, but does not contain the sodium bicarbonate found in the $CO_2$ sensor. Therefore, the pH is determined by the proton concentration in the conjunctival blood/tissue rather than having the proton concentration affected by the release of protons from the sodium bicarbonate due to interaction with $CO_2$. Thus, the pH sensor uses light absorption by a pH indicator solution, which is phenol red in the exemplary system. The phenol red is immobilized in a gel, (preferably polyacrylamide gel). As the proton concentration becomes higher, the phenol red dye turns yellow-orange in color, while at low proton concentration, the phenol red solution is dark red.

The gel provides a diffusion path for the protons so that the indicator solution in the gel equilibrates quickly with solution at the conjunctiva. Indeed, in a system in which a plurality of optical fibers are bundled within a microporous membrane, e.g., a polyethylene membrane, the diffusion path can be provided by gel that fills the microporous membrane and prevents bulk solution transport through the pores of the membrane.

To detect the changes in the indicator dye, light is transmitted through an optical fiber that is paired with a return fiber for detection. Both fibers are joined in a connector with a single optical fiber that extend to the detection region. In the exemplary system using phenol red, green light (e.g., pulses with a peak wavelength at 555 nm) are transmitted through the fiber. Red light pulses with peak wavelength of 660 nm are also transmitted through the fiber timed between the green pulses. The red light, which is unaffected by the indicator solution, is used as reference or control for changes in the optical efficiency of the system (caused by bending, for example). Such green and/or red light pulses can be provided using an LED. After passing through the indicator gel, the light that is not absorbed in the first pass is reflected back through the fiber and through the indicator gel by a mirror at the end of the fiber.

In this exemplary system, the conjunctival blood protons equilibrate with the indicator solution in the polyacrylamide gel. Increased acidity (low pH) results in higher transmission of green light due to decreased absorption. The return green light (along with return red reference light) passes along the optical fiber to the electro-optic connector, where approximately ½ of the light is transmitted along the detection optical fiber to a photo-detector. The ratio of the green light intensity to red light intensity provides a measure of the pH-dependent changes in the green light absorption that is independent of optical efficiency.

A number of other pH indicator dyes are available and can be used to construct spectrophotometric based pH sensors, e.g., using optical fibers. The selections of the wavelengths of light to use particular dye selections are understood by those skilled in the art, e.g., so that light with a wavelength at or near an absorption peak for the dye is used for signal generation, and control light, if used, is at a wavelength or range of wavelengths not substantially absorbed by the dye.

Temperature Sensor and Temperature Compensation of Measurements

It can also be beneficial to include a temperature sensor in a conjunctival monitor. Such a sensor can provide direct temperature monitoring. Such temperature monitoring can be used both as an indication of temperature at the eye, and also for correcting or normalizing other monitor measurements to a standard or selected temperature, for example, a temperature at which calibration of the sensors is carried out or to 37° C.

Temperature sensors can be constructed in various ways. One advantageous method utilizes a thermocouple, although other types of temperature measuring sensors can be used. A thermocouple is constructed of two different metals selected such that a small temperature-dependent voltage is generated at the junction of the two different metals. For use at the conjunctiva, the metals are sealed from contact with fluid.

An exemplary thermocouple uses a copper wire and a wire that is an alloy of copper and nickel alloy (constantan), twisted and welded together. While wires of various sizes can be used, for a conjunctival monitor the wires are preferably fine, e.g., 0.050 mm in diameter. The thermocouple is sealed from contact with liquid, preferably using a coating or sheath, such as a polyester sheath. This thermocouple provides good sensitivity over physiologically relevant temperatures. Preferably the temperature sensor has a precision of at least ±0.5° C. over the relevant range, more preferably at least ±0.3° C. over that range, and still more preferably at least ±0.1° C. In particular embodiments, the range over which the specified precision is provided includes at least a range 0.0° C. to 42° C., 20.0° C. to 42° C., or 20.0° C. to 40° C. Those skilled in the art are familiar with thermocouples, and with the selection of metals that will provide sensitivity over selected ranges.

Sensor Packaging

As the present sensors are intended to be used in a highly sensitive and vulnerable area of the body, it is highly preferred that at least the sensor tip be sterile. Such sterilization can be carried out by any method or combination of methods compatible with the sensor materials. Such methods include, for example, treatment with ethylene oxide gas, ultraviolet light, X-rays, gamma radiation, ethanol, wet or dry heat such as autoclave conditions, ozone, and the like. Those skilled in the art are familiar with the use of the various methods and the materials with which they are compatible. Standards for sterilization of medical devices are provided by ISO, ANSI, and/or AAMI (Association for the Advancement of Medical Instrumentation) standards. Highly preferably the sensor is sterilized according to the applicable standard(s).

The packaging and/or the sensor can include written indication that the sensor can be used adjacent to the conjunctiva, e.g., in the fornix. For example, the written indication can provide instructions on how the sensor is to be used. Written indication can be text and/or pictoral. Text can be in English and/or other languages such as German, French, Spanish, Italian, Japanese, and Chinese, without limitation.

In order to maintain sterility, it is useful to package the sensor, or at least the portion that will contact a patient, e.g., the sensor tip, in packaging that will maintain a sterile interior until opened. Any of the various packaging materials and methods can be used that are available for packaging sterile medical devices, such as disposable medical devices. These include, for example, paper or plastic pouches that block passage of microorganisms.

In keeping with the use of sterile sensors, it is beneficial to utilize sensors that are disposable, i.e., intended for single use, or are re-sterilizable. That is, the sensor can be sterilized before and/or after use to prepare it for at least one additional use.

Sensor Calibration

It is highly beneficial to calibrate monitors, including the present conjunctival monitors before use. This can be done using solutions that are equilibrated with gas mixtures of specified composition at controlled temperature. For example, calibration can be carried out using gas mixtures of carbon dioxide, oxygen, and nitrogen. Calibration can be carried out by any means suitable for the particular sensor construct.

For example, calibration can be carried out using three canisters, each containing different mixtures of carbon dioxide, oxygen, and nitrogen, and a sensor is calibrated against each of the 3 mixtures. During calibration, an individual sensor packaged in a sterile tonometer containing buffer solution is heated to 37° C. Each of the respective gas mixtures is passed through the tonometer equilibrating the buffer solution to the gas mixture (e.g., for ten minutes each). The electronic components associated with the sensor are then adjusted so that the system reading matches the known relative values and/or equilibrium concentration values. Preferably the supplying of the various gases or gas mixtures is performed automatically, with the flow from the gas canisters controlled by the monitor system. Preferably the sensor can be re-calibrated, e.g., if very long monitoring periods are involved.

Conjunctival Monitor System

One skilled in the art recognizes that, in this invention, sensors such as the blood/tissue gas and pH sensors described above are not used alone but form part of a monitoring system. The components of such a system will vary depending upon the particular sensors used. Typically, the system will include electronic and/or software components for converting a raw signal from the sensor to the respective physiological readings. Further, the system will typically have at least one output, for example, a display screen, printer, and/or a signal connection (such as a connection to a separate computer). In many cases a monitor system will also have data storage capability such as an electronic data storage device. In particular embodiments the system can store monitor data for at least 30 minutes, 1 hr, 2 hrs, 4 hrs, 6 hrs, 12 hrs, 24-hrs or even longer monitoring periods. It can be beneficial, e.g., for monitoring patients outside the immediate supervision of medical personnel, to have an alarm, such that the monitor will emit an alarm upon the occurrence of a particular condition. For example, the monitor can emit an alarm if the oxygen level drops below a pre-selected level and/or if the carbon dioxide level rises above a pre-selected level. Such an alarm can, for example, be audible and/or visual. Examples of visual alarms include flashing lights and symbols or text on a display alerting a person to the existence of the alarm triggering condition. Such alarms can be implemented in conventional ways, e.g., keyed to signal level from a sensor or to a calculated analyte level (for example, oxygen level).

This system will also typically include a source of electrical power, for example, standard line electricity or battery power. For systems that utilize conventional line electrical power, the systems may include a converter(s) to provide low voltage (and typically low amperage) power. Such low voltage power is typically 24 volts or less, 12 volts or less, 6 volts or less, 3 volts or less, or 1 volt or less.

Advantageously, the present conjunctival monitor systems can be constructed to be portable. Systems can be constructed to be adapted for rolling into place in a hospital or clinic setting, or to be carried, e.g., for use at out of hospital emergency sites or in emergency vehicles such as ambulances. For such non-hospital and non-clinic locations, preferably the system is battery powered, or otherwise uses a low voltage and/or direct current power (e.g., 3, 6, 12, or 24 volt electrical power).

Systems that utilize optical fiber sensors will also include a light source or sources configured to direct light through the optical fiber to a detection region of the fiber. Such light sources can be selected and/or the output light filtered to provide illumination of a particular wavelength or range of wavelengths as desired. Also when optical fiber sensors are used, the system will include photo detectors for detecting return light from the detection region of the fiber. The return light can be filtered in front of the photodetector to remove components of the return light that would interfere with the measurement.

In many electrical and/or electro-optic systems it is also advantageous if the temperature of at least some of the components is regulated. Such temperature regulation can be provided in a variety of ways (such as those conventional in the art) including, for example isolation of heat sources, provision of heat sources (e.g. electrical heater), use of heat sinks, use of refrigeration, and circulation of a temperature regulated liquid such as water. For example, it can be advantageous to regulate the temperatures of photo detectors.

For a practical system, it can also be advantageous for the sensor to be easily separable from the analysis and display unit. This can be accomplished utilizing conventional optical, electro-optical, and/or electrical connectors, or connectors specifically designed for the system. For a system utilizing optical fibers this can be conveniently accomplished utilizing connectors or a connection block which can be located at the display/analysis unit or remote from that unit. Such a connection block can abut optical fibers to couple light from the light source with the optical fibers of the sensor itself, as well as coupling the sensor optical fiber with the optical fiber leading to the photo detector. If electrical connections are required, such connections can also be made at such connector block or can be made at the display/analysis unit.

Use of Conjunctival Monitor

The conjunctival monitors as described herein allow monitoring of patients for an extended period of time, for example, periods of at least ½, 1, 2, 4, 6, 12 or 24-hours, or even longer.

To initiate monitoring the sensor tip is placed in the eye of the patient to be monitored, generally adjacent to the conjunctiva. While the sensor tip can be placed in various locations, an advantageous location is within the fornix. To increase the stability of the placement of the sensor tip, a sensor fibers and/or wires can be temporarily adhered to the patient e.g., taped to the face adjacent to the eye. The sensor can be connected to the monitor either before or after the sensor tip is placed in the eye. The monitoring can be continued for the desired period, e.g., through the duration of a particular medical procedure such as the surgery. The monitoring can be performed continuously or readings can be taken periodically or intermittently through the monitoring period. For example, readings can be taken only during a portion of a procedure in which it is expected that blood gases might fluctuate rather than during the entire duration of the procedure.

As indicated above, conjunctival monitoring using the present conjunctival sensors and monitor systems can be conducted in many different situations and settings. For example, monitoring can be carried out in hospital settings such as operating room, emergency room, intensive care unit, critical care unit, post-operative room, delivery room, and the like; in emergency transport situations such as in an ambulance; and at emergency locations, such as at accident sites, and at general residential and business sites (e.g., for heart attack and stroke victims). Likewise, conjunctival monitoring as described is suitable for essentially any person with an intact eye, including, for example, adults, neonates, children, and adolescents. Thus, the present methods and devices are broadly applicable for situations where information

EXAMPLES

Example 1

Use of Conjunctival Monitor in Dogs

As an initial test to determine whether an optical sensor could work in the conjunctiva, tests were performed in animal eyes. A sensor was used that has a heparin-coated, microporous polyethylene sheath around optical fibers for detection of pH, $CO_2$, and $O_2$, as well as a copper/constantin thermocouple for temperature measurement. The sensor had a diameter of approximately 0.5 mm. The sensor and the various constituent sensor fibers were constructed as exemplary sensor fibers described above, with rectangular holes arranged in a helical pattern at the tip of each fiber, where the holes contained the indicator chemistry.

Initially two dogs that were undergoing experimental placement of a vascular stent had an ocular sensor placed. The optical pH, $PO_2$, $PCO_2$, and temperature sensor two centimeters long was placed in the lower fornix of the eye, in contact with the conjunctiva. We discovered that the sensor accurately read the pH, carbon dioxide tension, and oxygen tension. The eyes were examined for any evidence of injury following monitoring, and none was found.

Example 2

Use of Conjunctival Monitor in Sheep

In a second test, several pregnant sheep that were undergoing various studies of hypoxia were used. The sensor was placed in the eye as in Example 1. Four sheep were studied and it was found that the sensor was able to monitor for over two hours without difficulty. We discovered that in these situations, where the physiology of the mother was not being manipulated, the values were stable. Again the eyes of the sheep were examined both before and after the study and no damage was noted.

Example 3

Use of Conjunctival Monitor in Pigs

In a third test, we studied several pigs undergoing bleeding experiments in a resuscitation model, to determine whether the sensor was capable of detecting changes in the physiologic milieu. A pig undergoing a 15% blood volume bleed had a sensor placed as above. The sensor monitoring showed that after the bleed the conjunctival tissue had a marked increase in carbon dioxide level and a fall off in oxygen tension. These values did not return to baseline following fluid resuscitation, suggesting that saline resuscitation is not an adequate substitution for blood.

The sensor also detected changes in pigs undergoing Extra Corporeal Membrane Oxygenation Therapy (ECMO), a form of cardiac bypass which is used in patients with severe cardiac and respiratory failure, when the therapy was interrupted. When the machine was disconnected, the sensor detected the resulting decrease in oxygen level and increase in carbon dioxide.

Example 4

Use of Conjunctival Monitor in Humans

Following the successful animal tests, human trials were performed. Approval was obtained from the Institutional Review Board (IRB) of a protocol that allowed placement of a sensor in the conjunctiva of patients undergoing general anesthesia for major surgical procedures. The protocol essentially consists of placing the sensor in the fornix of patients who are undergoing general anesthesia for an operative procedure. The sensor tip protrudes about 2 cm and rests in contact with the conjunctiva. The eye is taped closed. The sensor is calibrated prior to placement. All patients have an ophthalmologic exam both prior to placement, and following the removal of the sensor.

As with the animal monitoring described above, the conjunctival sensor used is a multiparameter sensor imbedded in a wire-like device less than 0.5 mm in diameter. Contained in it are sensors for pH, partial pressure of carbon dioxide, and partial pressure of oxygen, as well as temperature. The readings are determined by the interaction with the red, green, and blue fiberoptic light sources with the sensor indicators. The sensor and the various constituent sensor fibers were constructed as exemplary sensor fibers described above. The sensor is attached to a box (patient data module—PDM) which includes the data processor which contains the calibration constants and processes the signal which is then displayed on the monitor. The data is read and displayed continuously, both numerically and in graphic form displaying trends in the values. The sensor is packaged sterilely and is adapted for single patient use.

After approval of the protocol, patients were recruited for trial use of the conjunctival monitor. The majority of the patients tested had open heart procedures requiring cardiac bypass. These patients sustain major changes in their physiologic parameters because of the procedure that includes going on bypass, stoppage of the heart, the cardiac repair, coming off bypass and restarting the heart. The monitoring of two exemplary patients according to the approved protocol is described.

A. Exemplary Patient 1

52 year old woman with long standing history of cardiovascular disease underwent coronary artery bypass graft surgery.

The patient underwent the usual procedure for general anesthesia including intubation of the trachea and artificial ventilation. The conjunctival sensor (attached to the PDM) was introduced into the eye in contact with the conjunctiva after initiation of anesthesia, but prior to cannulation and placement on cardiac bypass. Following sensor insertion the usual procedure for initiating cardiac bypass was performed. Following placement on cardiac bypass the heart was stopped and the bypass of the obstructed vessels was performed. At the end of the procedure, three hours and seven minutes later, attempts were made to have the patient come off cardiac bypass. As this was unsuccessful, the patient was placed on a balloon pump to support her cardiac function.

Monitored values are obtained immediately after conjunctival sensor placement. According to the protocol, the sensor is left in place for the duration of the procedure or up to six hours, whichever is first. For this patient, the sensor was removed when the patient was placed on the balloon pump and prepared for transfer to the intensive care unit.

In this case, initial values for the conjunctival gas readings after 10 minutes of stabilization were pH 6.84/$PCO_2$ 44 Torr/$PO_2$ 33 Torr. As the coronary arteries were manipulated and bypass cannulation was attempted the carbon dioxide increased, the pH decreased gradually, and the oxygen values declined markedly. Gradually the carbon dioxide declined but the oxygen tension declined markedly to values as low as 5 Torr, which occurred at two hours and thirty-one minutes after insertion of the sensor. Monitor readings over the entire monitoring period are shown in FIG. 1. There was no injury to the eye upon opthalmic examination.

The conjunctival monitoring indicates that there was extremely low cerebral perfusion during this operation. The patient had decreased movements and difficulty with speech following the operation. There were no other findings suggesting that there were any problems during the surgery other than the low oxygen tension revealed by the conjunctival monitoring.

It is known that there can be many different causes of low cerebral persusion, which may include preexisting cerebral vascular disease, such as narrowing of the carotid arteries, and sometimes there can be obstruction of the cerebral vessels by the bypass cannulas. In addition, it is known that a significant number of patients undergoing arterial bypass during cardiac surgery have some cognitive defects (e.g., such as those observed for this patient) following the operation. Thus, the low oxygen tension observed using conjunctival monitoring may correlate with the observed cognitive defects, and so can provide information allowing a doctor to perform suitable intervention to increase oxygen tension.

B. Exemplary Patient 2

61 year old woman with long standing history of cardiovascular disease underwent coronary artery bypass graft surgery.

The surgery and conjunctival sensor placement were performed generally as for Patient 1 above. At the end of the procedure, two hours and thirty minutes after initial sensor placement, the patient come off cardiac bypass. Her heart was restarted and she came off bypass uneventfully. She had no obvious residual neurologic defects following the surgery.

Figure 2:
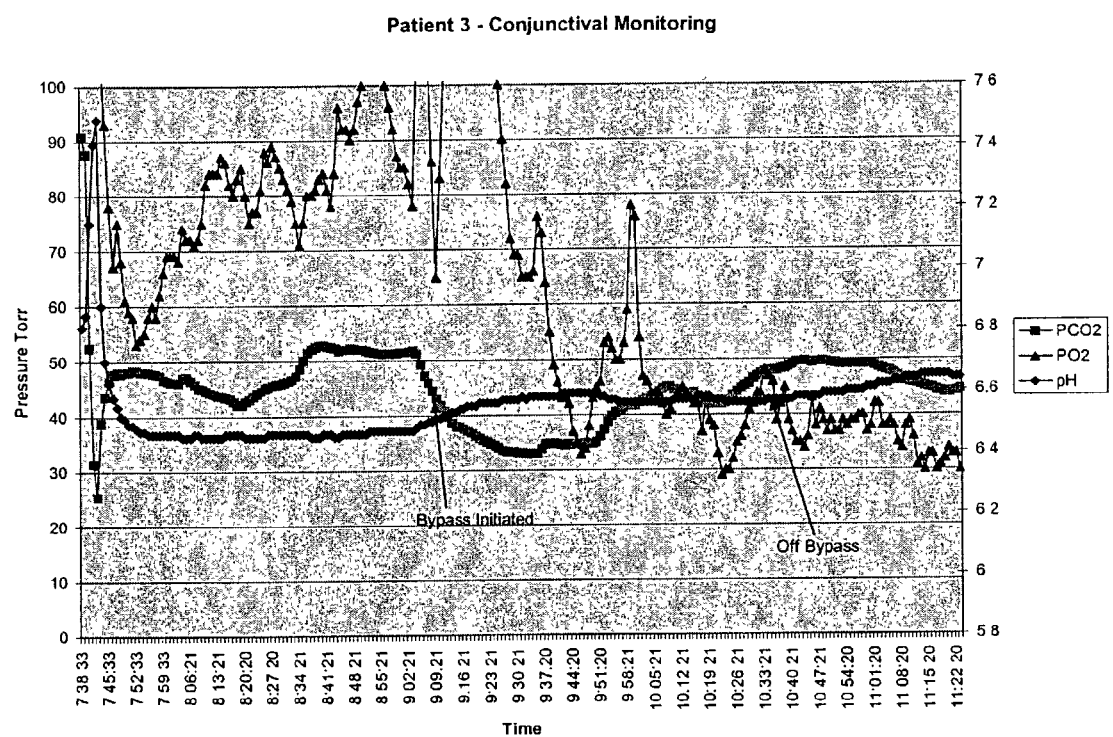
FIG. 2 is a graph showing the values for oxygen, carbon dioxide, and pH for exemplary patient 2, illustrating monitoring of typical oxygen values for cardiac bypass.

For this patient, initial values for the conjunctival gas readings after 10 minutes of stabilization were pH 7.30/$PCO_2$ 31 Torr/$PO_2$ 174 Torr. As the patient was placed on bypass the values changed somewhat to pH 7.46/$PCO_2$–25 Torr/$PO_2$–84 Torr. The patient came off the bypass at two hours and eighteen minutes with values of pH 7.33/$PCO_2$–33 Torr/$PO_2$–56 Torr. Monitor readings over the entire monitoring period are shown in FIG. 2. There was no injury to the eye upon opthalmic examination.

This patient demonstrated no clinically significant changes in the monitored conjunctival values during the surgery. She came off bypass without difficulty and on follow-up was doing well. In this case the monitoring demonstrated stability which correlated with a good outcome for the procedure.

Additional patients have been monitored similar to those described above.

Unless otherwise defined, all technical and scientific terms used herein have the same meaning as commonly understood by one of ordinary skill in the art to which this invention belongs. All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, other detection chemistries can be used in the sensors for detection of blood gases. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A method for monitoring blood and tissue gas or pH of a patient, comprising
    placing an optical blood and tissue gas monitor sensor tip adjacent to the palpebral or bulbar conjunctiva of said patient,
        wherein said sensor tip comprises at least one optical sensor fiber for detecting at least one blood and tissue gas or blood and tissue pH, and
        said sensor tip is connected with analysis and display components of a blood monitor system; and
        said sensor tip is adapted and configured to be held in place adjacent the palpebral or bulbar conjunctiva of the eye;
    determining patient blood and tissue gas or pH values or both with said blood monitor system; and
    recording or displaying said patient blood and tissue gas or pH values or both.

2. The method of claim 1, wherein said sensor tip has a detection length of 2 cm or less.

3. The method of claim 1, wherein said sensor tip further comprises an exterior biocompatible, microporous membrane containing at least two of a pH optical sensor fiber, a $PCO_2$ optical sensor fiber, and a $PO_2$ optical sensor fiber, wherein fluid flow trough said microporous membrane is inhibited.

4. The method of claim 3, wherein said sensor tip further comprises at least one distal terminal mirror that returns light through one or more of said optical sensor fibers.

5. The method of claim 4, wherein said sensor tip is 1.5 cm or less in length.

6. The method of claim 4, wherein said sensor tip is 1.0 cm or less in length.

7. The method of claim 3, wherein said fluid flow is inhibited by a gel.

8. The method of claim 7, wherein said gel comprises polyacrylamide gel.

9. The method of claim 3, wherein said sensor tip is coated with heparin.

10. The method of claim 3, wherein said optical sensor fibers comprise acrylic optical fibers.

11. The method of claim 1, wherein said monitoring is conducted during treatment of said patient.

12. The method of claim 11, wherein said treatment comprises surgery.

13. The method of claim 12, wherein said surgery comprises heart surgery.

14. The method of claim 12, wherein said surgery comprises lung surgery.

15. The method of claim 11, wherein said treatment comprises injection or infusion of a drug.

16. The method of claim 11, wherein said monitoring is performed for a period of at least one hour.

17. The method of claim 1, wherein said sensor tip further comprises a pH optical sensor fiber, a $PCO_2$ optical sensor fiber, and a $PO_2$ optical sensor fiber.

18. The method of claim 17, wherein said sensor tip further comprises a temperature sensor.

19. The method of claim 18, wherein said temperature sensor comprises a thermocouple.

20. The method of claim 19, wherein temperature readings from said temperature sensor are used to normalize readings for one or more of pH, $CO_2$, and $O_2$.

21. The method of claim 17, wherein said pH optical sensor fiber comprises phenol red in polyacrylamide gel, and said fiber is perforated.

22. The method of claim 17, wherein said $PCO_2$ optical sensor fiber comprises phenol red in bicarbonate solution, and said fiber is perforated.

23. The method of claim 17, wherein said $PO_2$ optical sensor fiber comprises ruthenium dye in a silicone matrix, and said fiber is perforated.

24. The method of claim 17, wherein said pH optical sensor fiber comprises phenol red in polyacrylamide gel, said $PCO_2$ optical sensor fiber comprises phenol red in bicarbonate solution, and said $PO_2$ optical sensor fiber comprises ruthenium dye in a silicone matrix, and said fibers are perforated.

25. The method of claim 24, wherein said blood monitor system comprises a light source and photodetectors.

26. The method of claim 25, wherein green light pulses are used for detection and red light pulses are used for reference in said pH and $PCO_2$ optical sensor fibers, and blue light is used for detection and green light is used for reference in said $PO_2$ optical sensor fiber.

27. The method of claim 1, wherein said monitoring is performed on a patient in an emergency room.

28. The method of claim 1, wherein said monitoring is performed in an intensive care unit.

29. The method of claim 1, wherein said monitoring is performed in an emergency transport vehicle.

30. A conjunctival monitor comprising a sensor comprising a sensor tip with a detection length of 2 cm or less adapted and configured to fit adjacent to the palpebral or bulbar conjunctiva of a patient's eye, and adapted and configured to be held in place adjacent the palpebral or bulbar conjunctiva of the eye, wherein said sensor tip comprises at least one optical sensor fiber for detecting at least one blood or tissue parameter, and said sensor tip is connected with analysis and display components of a blood monitor system.

31. The conjunctival monitor of claim 30, wherein said sensor tip further comprises an exterior biocompatible, microporous membrane containing at least two of a pH optical sensor fiber, a $PCO_2$ optical sensor fiber, and a $PO_2$ optical sensor fiber, wherein fluid flow through said microporous membrane is inhibited.

32. The conjunctival monitor of claim 31, wherein said fluid flow is inhibited by a gel.

33. The conjunctival monitor of claim 32, wherein said gel comprises polyacrylamide gel.

34. The conjunctival monitor of claim 31, wherein said sensor tip is coated with heparin.

35. The conjunctival monitor of claim 31, wherein said optical sensor fibers comprise acrylic optical fibers.

36. The conjunctival monitor of claim 31, wherein said pH optical sensor fiber comprises phenol red in polyacrylamide gel, and said fiber is perforated.

37. The conjunctival monitor of claim 31, wherein said $PCO_2$ optical sensor fiber comprises phenol red in bicarbonate solution, and said fiber is perforated.

38. The conjunctival monitor of claim 31, wherein said $PO_2$ optical sensor fiber comprises ruthenium dye in a silicone matrix, and said fiber is perforated.

39. The conjunctival monitor of claim 31, wherein said pH optical sensor fiber comprises phenol red in polyacrylamide gel, said $PCO_2$ optical sensor fiber comprises phenol red in bicarbonate solution, and said $PO_2$ optical sensor fiber comprises ruthenium dye in a silicone matrix, and said fibers are perforated.

40. The conjunctival monitor of claim 39, wherein green light pulses are used for detection and red light pulses are used for reference in said pH and $PCO_2$ optical sensor fibers, and blue light is used for detection and green light is used for reference in said $PO_2$ optical sensor fiber.

41. The conjunctival monitor of claim 30, wherein said sensor tip further comprises at least one distal terminal mirror that returns light through one or more of said optical sensor fibers.

42. The conjunctival monitor of claim 30, wherein said detection length is 1.5 cm or less.

43. The conjunctival monitor of claim 30, wherein said detection length is 1.0 cm or less.

44. The conjunctival monitor of claim 30, wherein said sensor tip further comprises a pH optical sensor fiber, a $PCO_2$ optical sensor fiber, and a $PO_2$ optical sensor fiber.

45. The conjunctival monitor of claim 30, wherein said sensor tip further comprises a temperature sensor.

46. The conjunctival monitor of claim 45, wherein said temperature sensor comprises a thermocouple.

47. The conjunctival monitor of claim 46, wherein temperature readings from said temperature sensor are used to normalize readings for one or more of pH, $CO_2$, and $O_2$.

48. The conjunctival monitor of claim 30, wherein said blood monitor system further comprises a light source and one or more photodetectors.

49. The conjunctival monitor of claim 30, wherein the blood monitor system further comprises an analysis unit that processes signals from said sensor tip and converts said signals into output representative of blood gas or blood pH values or both.

50. The conjunctival monitor of claim 49, wherein the blood monitor system further comprises a display unit for displaying output for blood gas or blood pH values or both.

51. The conjunctival monitor of claim 30, further comprising a written indication that said monitor or said sensor can be used for conjunctival monitoring.

52. A kit consisting essentially of
a disposable sensor for a conjunctival monitor, comprising
a sensor tip comprising at least two of a pH sensor fiber or electrode, a $PCO_2$ sensor fiber or electrode, and a $PO_2$ sensor fiber or electrode,
wherein said sensor tip has a thickness of 0.5 mm or less,
said sensor tip can be connected with analysis and display components of a blood monitor system, and
said sensor tip is adapted and configured to be held in place adjacent the palpebral or bulbar conjunctiva of the eye;
a sterile packaging enclosing at least the portion of said sensor tip that contacts the conjunctiva of a patient during use; and
a written indication for use of said sensor for conjunctival monitoring.

53. The sensor of claim 52, wherein said sensor tip further comprises an exterior biocompatible, microporous membrane containing said sensor fibers or electrodes, wherein fluid flow through said microporous membrane is inhibited.

54. The sensor of claim 53, wherein said sensor tip further comprises an $PCO_2$ optical sensor fiber, and a $PO_2$ optical sensor fiber.

55. The sensor of claim 54, wherein said sensor tip further comprises a pH optical sensor fiber and a thermocouple for temperature determination.

56. The sensor of claim 55, wherein said sensor tip has a detection length of 2 cm or less.

57. The sensor of claim 55, wherein said sensor tip has a detection length of 1.5 cm or less.

58. The sensor of claim 52, where said written indication is on said sterile packaging.

* * * * *